United States Patent
Bryant et al.

(10) Patent No.: US 9,794,168 B2
(45) Date of Patent: Oct. 17, 2017

(54) SCALABLE CONTINUITY TEST FOR A GROUP OF COMMUNICATION PATHS

(71) Applicant: CISCO TECHNOLOGY, INC., San Jose, CA (US)

(72) Inventors: Stewart Frederick Bryant, Surrey (GB); Carlos M. Pignataro, Raleigh, NC (US); George Swallow, Boston, MA (US)

(73) Assignee: Cisco Technology, Inc., San Jose, CA (US)

( * ) Notice: Subject to any disclaimer, the term of this patent is extended or adjusted under 35 U.S.C. 154(b) by 169 days.

(21) Appl. No.: 14/819,346

(22) Filed: Aug. 5, 2015

(65) Prior Publication Data

US 2017/0041219 A1  Feb. 9, 2017

(51) Int. Cl.
*H04L 12/703* (2013.01)
*H04L 12/723* (2013.01)

(52) U.S. Cl.
CPC .............. *H04L 45/28* (2013.01); *H04L 45/50* (2013.01)

(58) Field of Classification Search
CPC ......... H04L 45/28; H04L 45/50; H04L 45/68; H04L 45/00; H04L 12/4641
See application file for complete search history.

(56) References Cited

U.S. PATENT DOCUMENTS

| 9,049,233 | B2 | 6/2015 | Frost et al. |
| 9,131,015 | B2 | 9/2015 | Rittle et al. |
| 2009/0116395 | A1* | 5/2009 | Sasaki ..................... H04L 43/50 370/245 |
| 2012/0224583 | A1* | 9/2012 | Sergeev ................ H04L 12/413 370/395.5 |
| 2013/0259057 | A1 | 10/2013 | Dutta |

OTHER PUBLICATIONS

IETF RFC 6391, "Flow-Aware Transport of Pseudowires over an MPLS Packet Switched Network", S. Bryant et al., Nov. 2011.
IETF RFC 4447, "Pseudowire Setup and Maintenance Using the Label Distribution Protocol (LDP)", L. Martini et al., Apr. 2006.

* cited by examiner

*Primary Examiner* — Ayaz Sheikh
*Assistant Examiner* — Debebe Asefa
(74) *Attorney, Agent, or Firm* — Cindy Kaplan (57) ABSTRACT

In one embodiment, a method includes generating at a network device, a continuity test packet configured to pass through a set of communication paths terminating at the network device and at least one other network device located at an opposite end of the communication paths, transmitting at the network device the continuity test packet on a first communication path in the set of communication paths, and identifying at the network device a failure in the set of communication paths if the continuity test packet is not received on a last communication path in the set of communication paths. An apparatus and logic are also disclosed herein.

20 Claims, 5 Drawing Sheets

SCALABLE CONTINUITY TEST FOR A GROUP OF COMMUNICATION PATHS

TECHNICAL FIELD

The present disclosure relates generally to communications networks, and more particularly, to continuity tests for communication paths.

BACKGROUND

A network device in a communication network may terminate a very large number of communication paths (physical or virtual), which may lead to scaling problems when attempting to run continuity tests on the communication paths.

BRIEF DESCRIPTION OF THE DRAWINGS

Corresponding reference characters indicate corresponding parts throughout the several views of the drawings.

DESCRIPTION OF EXAMPLE EMBODIMENTS

Overview

In one embodiment, a method generally comprises generating at a network device, a continuity test packet configured to pass through a set of communication paths terminating at the network device and at least one other network device located at an opposite end of the communication paths, transmitting at the network device the continuity test packet on a first communication path in the set of communication paths, and identifying at the network device a failure in the set of communication paths if the continuity test packet is not received on a last communication path in the set of communication paths.

In another embodiment, an apparatus generally comprises a plurality of interfaces for communication with a plurality of communication paths terminating at the apparatus and at least one other network device located at an opposite end of the communication paths and a processor for generating a continuity test packet configured to pass through the set of communication paths, transmitting the continuity test packet on a first communication path in the set of communication paths, and identifying a failure in the set of communication paths if the continuity test packet is not received on a last communication path in the set of communication paths.

EXAMPLE EMBODIMENTS

The following description is presented to enable one of ordinary skill in the art to make and use the embodiments. Descriptions of specific embodiments and applications are provided only as examples, and various modifications will be readily apparent to those skilled in the art. The general principles described herein may be applied to other applications without departing from the scope of the embodiments. Thus, the embodiments are not to be limited to those shown, but are to be accorded the widest scope consistent with the principles and features described herein. For purpose of clarity, details relating to technical material that is known in the technical fields related to the embodiments have not been described in detail.

When a large number of communication paths (physical or virtual) are concentrated and terminated at a network device, it may be difficult to test connection continuity for all of the communication paths. For example, if individual sessions need to be created for each communication path and packets continuously sent across each communication path to test continuity, this would significantly add to the OAM (Operations, Administration, and Maintenance) overhead.

In pseudowire systems for example, a network device (e.g., TPE (Terminating Provider Edge)) may terminate a very large number of pseudowires, which may lead to scaling problems when attempting to run circuit connectivity tests at the pseudowire layer. Similar problems exist in many other environments using virtual or physical communication paths.

The embodiments described herein build a set of concatenated communication paths and perform a connection continuity (circuit connectivity) (CC) test on the set of communication paths with a single packet, thereby reducing the OAM processing overhead. The embodiments may be used, for example, to perform a test on a forwarding plane of a pseudowire network, MPLS (Multi-Protocol Label Switching) VPN (Virtual Private Network), or any other type of network, without incurring excessive loading of the OAM subsystem. One or more embodiments significantly improve scaling properties of dataplane circuit connectivity tests.

Figure 1:
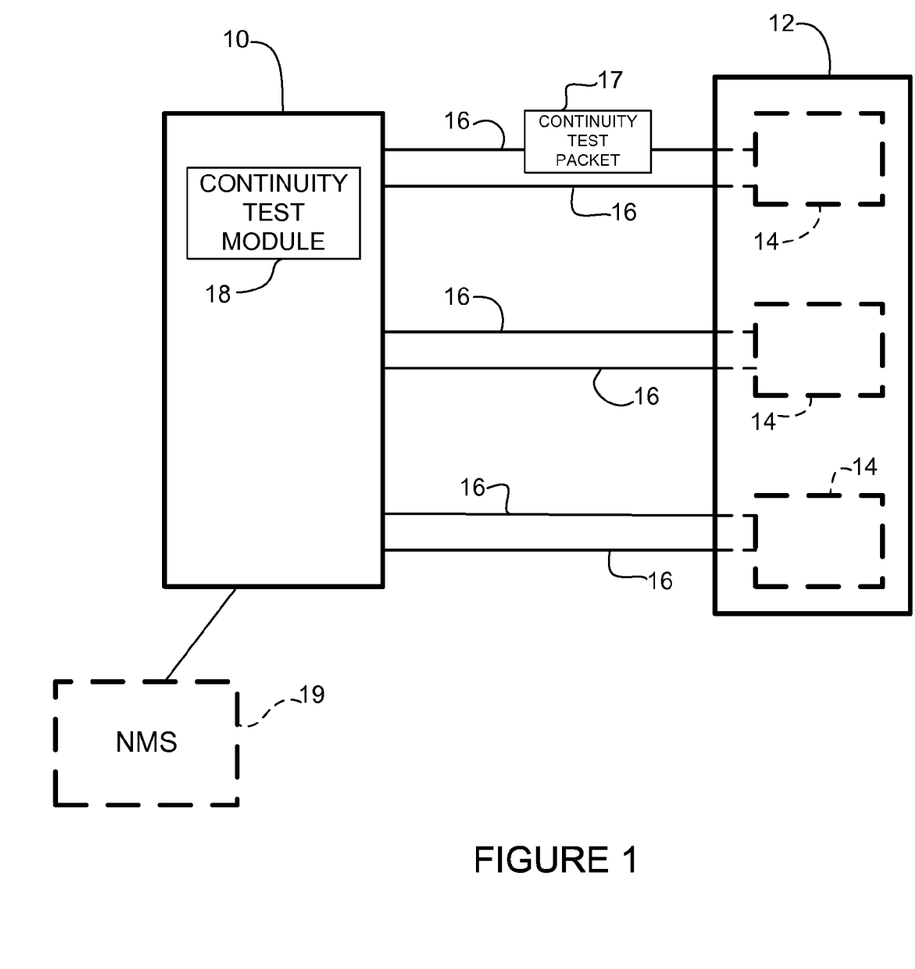
FIG. 1 illustrates an example of a network in which embodiments described herein may be implemented.

Referring now to the drawings, and first to FIG. 1, a network in which embodiments described herein may be implemented is shown. The embodiments operate in the context of a data communication network including multiple network devices. For simplification, only a small number of nodes and communication paths are shown. The network may include any number of network devices in communication via any number of nodes (e.g., routers, switches, controllers, gateways, access layer devices, aggregation layer devices, edge devices, core devices, or other network devices), which facilitate passage of data within the network.

The network shown in the example of FIG. 1 includes nodes 10, 12 connecting a plurality of communication paths 16. In one example, nodes 10, 12 terminate pseudowires 16 and may comprise TPEs. In another example, node 10 may be a hub TPE in communication with a plurality of spokes 14 (e.g., hub and spoke VPN (Virtual Private Network)). The nodes 10, 12 may also comprise a wireless access point and controller or nodes in a DOCSIS (Data over Cable Service Interface Specification) implementation. In one example, the nodes 10, 12 may be equipment located on separate racks in a building. It is to be understood that these are only examples and any network device including, routers, switches, gateways, controllers, access points, or any other tunnel end point or node operable to terminate a large number of communication paths 16 may be used.

The communication paths 16 may be physical communication paths or virtual communication paths. For example, the communication paths (links) 16 may comprise one or more link bundles, pseudowire groups, optical fibers, tunnels, Label Switched Paths (LSPs), or any other parallel or closely coupled communication paths. In one example, the communication paths 16 comprise pseudowires (e.g., emulated circuits). Functions provided by the pseudowire include encapsulating bit streams, cells, or PDUs (Protocol Data Units) arriving at an ingress port and carrying them across a path or tunnel, and other operations that emulate the behavior and characteristics of a particular service. In another example, the communication paths comprise tunnels (e.g., MPLS-TE (Multi-Protocol Label Switching Traffic Engineering), SR-TE (Segment Routing Traffic Engineering), IP (Internet Protocol), IPsec (Internet Protocol Security), etc.). In yet another example, the communication paths comprise hierarchical LSPs. It is to be understood that the communication paths described herein are only examples and that the embodiments may be used to perform continuity checks on other types of communication paths connecting any type of network devices.

In one example, the communication paths 16 may be used to transfer data across a Packet Switched Network (PSN), such as a Multi-Protocol Label Switching (MPLS) network. In the MPLS network, packets are assigned labels by Label Switching Routers (LSRs) and forwarded along a Label Switched Path (LSP). In one example, multiple communication paths may share the same LSP.

In certain embodiments, one or more of the nodes 10, 12, 14 comprise a continuity test module 18. As described in detail below, the continuity test module 18 builds a snake of concatenated communication paths 16 and performs a circuit continuity test on the set of communication paths. In one embodiment, a single packet (continuity test packet 17) is used to reduce OAM processing overhead. In other embodiments concurrent checks are performed on multiple sets of communication paths to further isolate a failure. In this case, multiple packets (e.g., two or three) may be used to test a group of communication paths. The continuity tests may be run continuously or periodically.

One or more of the network devices 10, 12 may be in communication with a network management station (NMS) 19 operable to initiate the continuity test at the network device. In another embodiment, a coordination protocol is used between the nodes 10, 12 to coordinate the continuity test. In either embodiment, results of the continuity test may be transmitted to the network management station 19 or other network device. For example, the node 10 may alert the NMS 19 of a failure at the one of the communication paths 16.

It is to be understood that the network shown in FIG. 1 is only an example and the embodiments described herein may be implemented in networks comprising different network topologies or network devices, or using different network protocols, without departing from the scope of the embodiments. For example, there may be any number or types of communication paths 16 running between the network devices 10 and 12 (or 10 and 14). Also, there may be any number or type of network devices terminating the communication paths or intermediate nodes interposed between the network devices.

Figure 2:
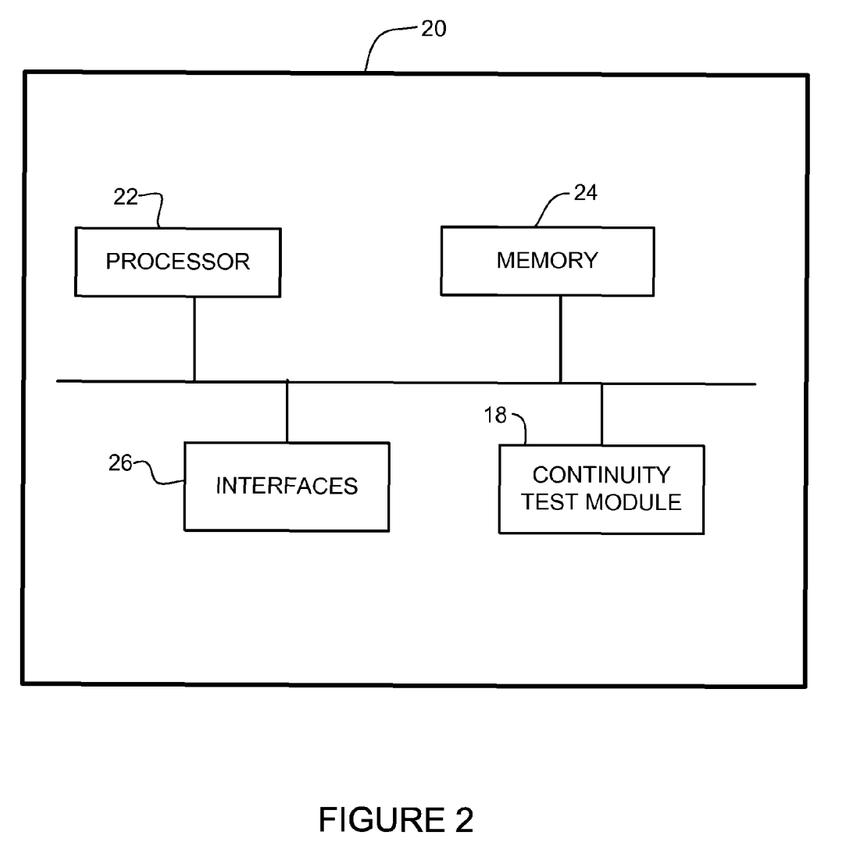
FIG. 2 depicts an example of a network device useful in implementing embodiments described herein.

FIG. 2 illustrates an example of a network device 20 (e.g., node 10 in FIG. 1) that may be used to implement the embodiments described herein. In one embodiment, the network device 20 is a programmable machine that may be implemented in hardware, software, or any combination thereof. The network device 20 includes one or more processor 22, memory 24, network interfaces 26, and continuity test module 18.

Memory 24 may be a volatile memory or non-volatile storage, which stores various applications, operating systems, modules, and data for execution and use by the processor 22. For example, components of continuity test module 18 (e.g., code, logic, software, firmware, etc.) may be stored in memory 24. Memory may also store a platform label table mapping labels to network locations or routes.

Logic may be encoded in one or more tangible media for execution by the processor 22. The processor 22 may be configured to implement one or more of the functions described herein. For example, the processor 22 may execute codes stored in a computer-readable medium such as memory 24 to perform the process described below with respect to FIG. 3. The computer-readable medium may be, for example, electronic (e.g., RAM (random access memory), ROM (read-only memory), EPROM (erasable programmable read-only memory)), magnetic, optical (e.g., CD, DVD), electromagnetic, semiconductor technology, or any other suitable medium. In certain embodiments, logic may be encoded in non-transitory computer-readable media.

The network interfaces 26 may comprise any number of interfaces (linecards, ports) for receiving data or transmitting data to other devices. As shown in FIG. 1, the nodes 10, 12 may comprise interfaces for transmitting or receiving the continuity test packet 17 on communication paths 16. The network interface 26 may include, for example, an Ethernet interface for connection to a computer or network. The network interfaces 26 may be configured to transmit or receive data using a variety of different communication protocols. The interfaces 26 may include mechanical, electrical, and signaling circuitry for communicating data over physical communication paths coupled to the network. The interfaces 26 may also comprise virtual interfaces for communicating data over virtual communication paths 16. For example, a virtual interface representation of a PW may be provided at a TPE at one end of the virtual link (communication path) and on another TPE at an opposite end of the virtual link (communication path), as shown in FIG. 1.

It is to be understood that the network device 20 shown in FIG. 2 and described above is only an example and that different configurations of network devices may be used. The network device 20 may further include any suitable combination of hardware, software, algorithms, processors, devices, modules, components, or elements operable to facilitate the capabilities described herein.

Figure 3:
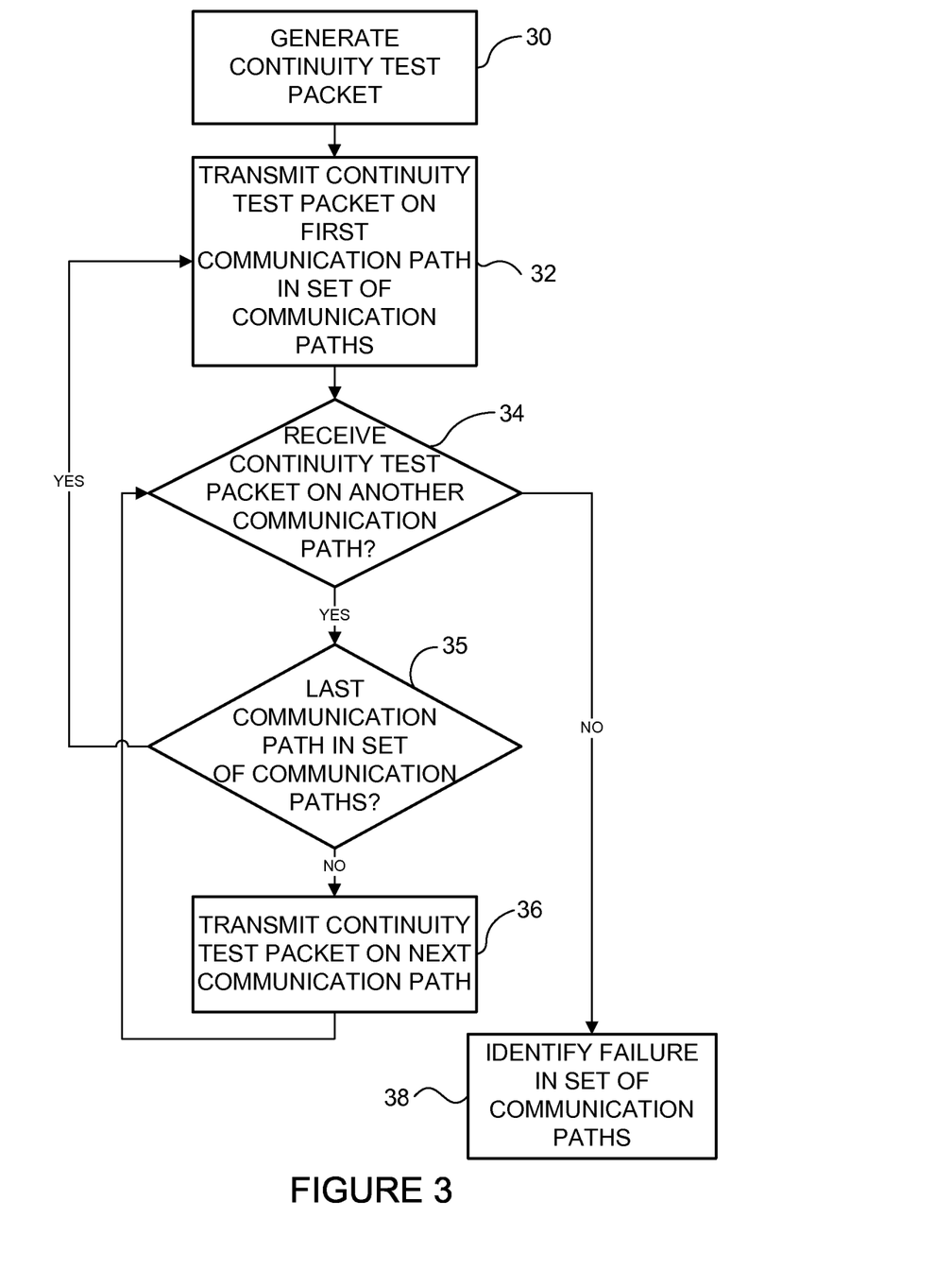
FIG. 3 is a flowchart illustrating an overview of a process for performing a continuity test for a plurality of communication paths, in accordance with one embodiment.

FIG. 3 is a flowchart illustrating an overview of a process for performing a continuity test on a set of communication paths, in accordance with one embodiment. At step 30, a network device (e.g., node 10 in FIG. 1) generates a continuity test packet 17 configured to pass through a set of communication paths 16 terminating at the network device 10 and at least one other network device (e.g., node 12 or nodes 14 in FIG. 1) located at an opposite end of the communication paths. The network device 10 transmits the continuity test packet 17 on a first communication path towards the other network device 12 (step 32). If the network device 10 receives the continuity test packet on another communication path (step 34) and the communication path is not the last communication path in the set of communication paths (step 35), it continues to forward the packet onto the next communication path back towards the other node 12 (step 36). If the communication path is the last communication path in the set of communication paths (step 35), all communication paths passed the continuity test and the network device can begin another connection continuity check by transmitting another continuity test packet (step 32) (either immediately or after a delay). The term 'last communication path' as used herein may refer to any of the communication paths in the set of communication paths that the test packet is configured to pass through last. For example, the last communication path may correspond to a label at a bottom of a label stack in the continuity test packet 17. In one example, the network device 10 knows that the packet was received on the last communication path since the label has a BoS (Bottom of Stack) bit set, as described below. If the network device 10 does not receive the continuity test packet 17 back from the other node 12 at any point during the continuity test, a failure in the set of communication paths 16 is identified (step 38). Additional tests may be performed to isolate the failure and identify the failed communication path, as described below.

It is to be understood that the process shown in FIG. 3 and described above is only an example and steps may be added, modified, reordered, or combined, without departing from the scope of the embodiments. Also, it may be noted that the processor 22 shown in FIG. 2 or the continuity test module 18 shown in FIG. 1 (or a combination thereof) may implement one or more of the steps shown in FIG. 3 and described herein. For example, logic encoded on a computer readable media and executed by the processor 22 may be operable to perform one or more steps shown in FIG. 3 and described herein.

Figure 4:
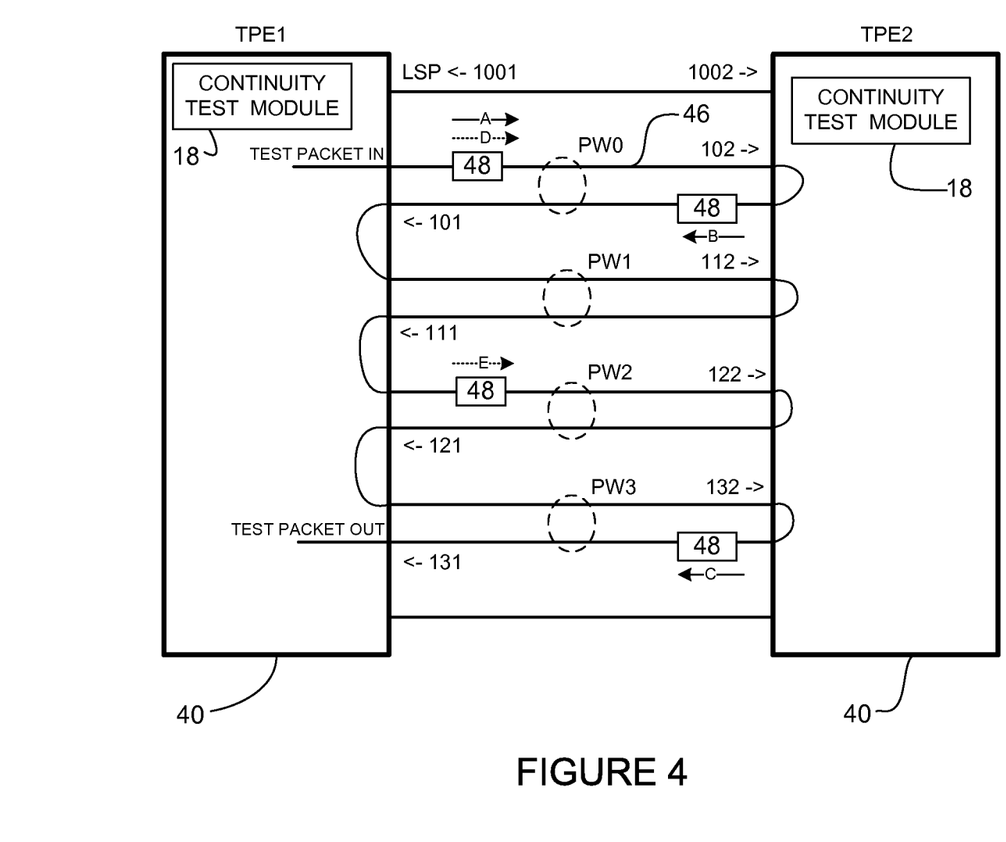
FIG. 4 illustrates a continuity test on a plurality of pseudowires, in accordance with one embodiment.

FIG. 4 illustrates an example in a pseudowire context, and more specifically pseudowire over MPLS, in accordance with one embodiment. In this example, there are four PWs (communication paths 46) (PW0, PW1, PW2, PW3) terminating at TPE nodes 40 (TPE1, TPE2). The label that TPE2 uses to identify PW0 is 102 and the label that TPE1 uses to identify PW0 is 101. As shown in FIG. 4, the label that TPE2 uses to identify PW1 is 112, PW2 is 122, and PW3 is 132. The label that TPE1 uses to identify PW1 is 111, PW2 is 121, and PW3 is 131.

The PWs (PW0, PW1, PW2, and PW3) are concatenated as shown in FIG. 4 in order to test the pseudowires in batches without a control plane (or a management system) involved individually in each PW test. This method is referred to herein as 'snaking' and enables scaling of the continuity tests.

In one embodiment, a change is made to the PW design so that a PW with the BoS (Bottom of Stack) bit set is processed as normal, but a PW with the BoS bit clear is popped and the packet forwarded according to the next label. The labels used by the continuity tests are preferably located in a platform label table at the TPEs 40. The TPEs 40 preferably perform recursive forwarding in which they look at the outgoing PW label, see what LSP they need to send it over, and push the corresponding LSP label.

The following describes an example for building a label stack so that continuity test packet 48 travels along the set of PWs to be tested (i.e., through each of the communication paths 46 in the set of communication paths).

Continuity test packet 48 sent at A in FIG. 4 includes the following label stack:

1002, 102, 101, 112, 111, 122, 121, 132, 131, ACH (Associated Channel Header), CC (Circuit Connectivity) payload In this example, 1002 is the LSP to TPE2, 102 is the PW0 in direction TPE1 to TPE2, 101 is PW0 in the direction TPE2 to TPE1. The packet 48 on path A is generated by TPE1 and used to start the continuity test process. In this example, the packet 48 comprises the LSP label to TPE2, the set of PW labels needed to walk the packet back and forth through the set of communication paths, the ACH, and the CC OAM payload.

At TPE2, the LSP label (1002) is popped. TPE2 then notes that the PW label 102 does not have BoS set, so that is also popped. The next label in the label stack is PW label 101. TPE2 determines (e.g., by performing a lookup in a label table) that the way to deliver a packet with label 101 is to push LSP label 1001. TPE2 uses this information to forward the packet at B to TPE1. The packet 48 forwarded at B includes the following label stack:

1001, 101, 112, 111, 122, 121, 132, 131, ACH, CC payload In this example, 1001 is the LSP to TPE1 and 101 is the PW0 in direction TPE2 to TPE1. The packet further includes the set of PW labels needed to walk the packet back and forth, the ACH, and the CC OAM payload.

This process continues until TPE1 receives packet 48 on the last communication path in the set of communication paths. The packet transmitted at C in FIG. 4 includes the following label stack:

1001, 131, ACH, CC payload

Label 131 is a PW with the BoS bit set, therefore the ACH is processed, and TPE1 is able to determine that the continuity test (snaking) packet 48 successfully arrived and that PW0 through PW3 have connectivity.

In the above example, the continuity test packet 48 was configured to transverse the pseudowires in order (e.g., PW0, PW1, PW2, PW3). It is to be understood that the packet may run through the communication paths in any order (e.g., random, specified pattern, etc.).

It may also be noted that the PWs in the test group do not all need to travel over the same LSP, nor do they all need to terminate on the same node.

The following describes an example of an embodiment that may be used to isolate a failure when the continuity test packet is not received on the final (last) communication path. In the above example, when any PW fails, the packet shown on path C is never received. TPE1 may try to send another test packet one or more times, or it may, without significant penalty, go directly to diagnostic mode.

In one example, TPE1 first uses a binary chop to split the PW list in half, construct two continuity test packets, and transmit both packets. For example, as shown in FIG. 4, TPE1 may generate and transmit two test packets 48 generally simultaneously at D (PW0) and E (PW2). TPE1 does not need to know much about the PWs, therefore this can be delegated to a low level process. In the example shown in FIG. 4, the packet sent at D covers the set of communication paths PW0 and PW1 and includes the following label stack:

1002, 102, 101, 112, 111, ACH, CC payload

The packet sent at E covers the set of communication paths PW2 and PW3 and includes the following label stack:

1002, 122, 121, 132, 131, ACH, CC payload

In this example PW3 fails, thus the packet transmitted at D gets through, but the packet transmitted at E does not get through. The path traversed by the packet transmitted at E can then be further investigated, as described below.

The following example looks at a set of 16 PWs (PW0 ... PW15) with a failure at PW14. In this example, the continuity test covers the following sets of PWs:

(a) [0 ... 15]→this check fails due to failure at PW14;
    (b) [0 ... 7], [8 ... 15]→8 ... 15 fails
    (c) [0 ... 7], [8 ... 11], [12 ... 15]→12 ... 15 fails
    (d) [0 ... 11], [12, 13], [14, 15]→14, 15 fails
    (e) [0 ... 13], [14], [15]→14 fails
    (f) [0 ... 13, 15]→continue to test remaining PWs.

In the process described above, (a) is the first test of the set of PWs (PW0 through PW15), which fails due to a failure at PW14. In (b), (c), (d), and (e) a series of tests are conducted to diagnose the cause of the failure. During these tests, the validated PWs may continue to be tested as a group in case of further failure. For example, the communication paths that passed the test may be tested in one set, while the remaining communication paths are split into two sets for additional testing. As shown above, the test at (b) splits the first set 0→15 into two sets, 0→7 and 8→15. Since the failure is at PW14, the second set (8→15) fails. At (c) the set containing 8→15 is broken down further into two sets (8→11 and 12→15]. The PWs that were not in the failed set are added to the communication paths (known operating communication paths) that have previously passed the continuity test. At (e), the failure is identified at PW14. The continuity test module 18 continues to the test the remaining PWs [0→13, 15] at (f). In the above example no more than three OAM packets would need to be sent. A fault is identified in $\log_2$ n round trip times+processing time.

It is to be understood that the process described above to isolate the failure is only an example and that other search strategies may be used, without departing from the scope of the embodiments.

Figure 5A:
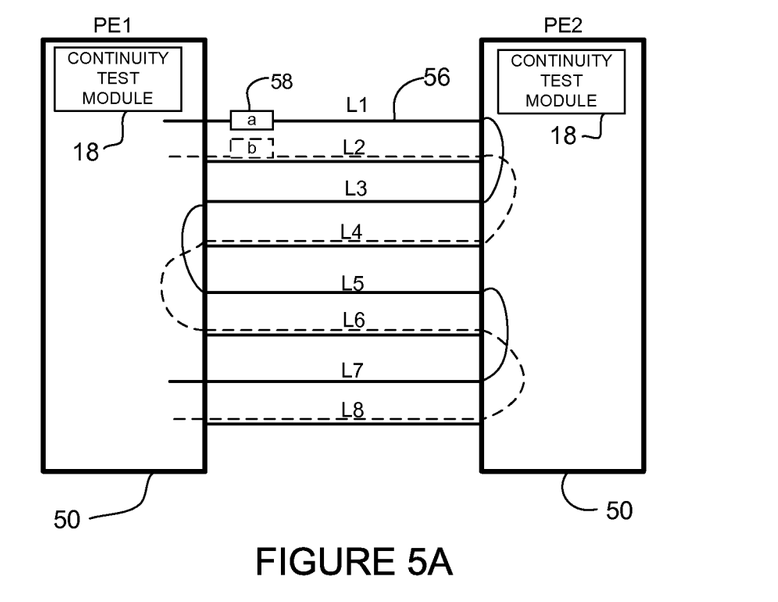
FIG. 5A illustrates concurrent probes for continuity testing a group of communication paths, in accordance with one embodiment.

In the above examples, the focus was one of equally dividing m pseudowires by n probes to choose the size of the 'snake'. As shown in FIG. 5A, this results in two packets 58 (a, b), each packet traversing half of the communication paths 56 between nodes 50 (PE1, PE2). In the example shown in FIG. 5A, packet (a) traverses communication paths (links) L1, L3, L5, and L7 and packet (b) traverses communication paths L2, L4, L6, and L8. As noted above, the packets may pass through the communication paths in any order and any combination of communication paths may be included in each set of communication paths.

Figure 5B:
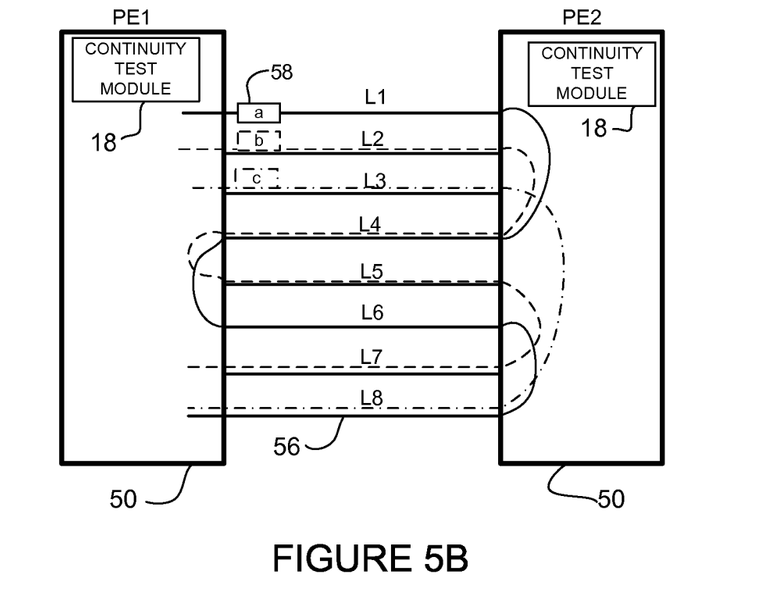
FIG. 5B illustrates overlapping concurrent probes for continuity testing a group of communication paths, in accordance with one embodiment.

The node 50 may support a number of n concurrent 'snake-probes', with a number of m pseudowires, with m larger than (or much larger than) n. In one or more embodiments, a strategy of correlation may be used. For example, a number of PWs per snake may be chosen that is larger than m/n. This results in some overlap between the test groups, as shown in FIG. 5B. In the example illustrated in FIG. 5B, packet (a) tests communication paths L1, L4, L6, and L8, packet (b) tests communication paths L2, L4, L5, and L7, and packet (c) tests communication paths L3 and L8. If packet (b) is returned but not packets (a) and (c), it is known that there is a failure in link (communication path) L8 (assuming a single failure). Similarly, if packets (a) and (c) are returned, but not packet (b), then it is known that there is a failure on link L2, L5, or L7. Further test packets may be sent to identify the failed link. When there are two snake probes testing the same link (e.g., L4 and L8 in FIG. 5B), the PE 50 may correlate failure state of the communication paths.

In another example comprising a group of 24 pseudowires, a continuity test packet (a) tests PW1-PW10, packet (b) tests PW8-PW18, and packet (c) tests PW16-PW24. Consequently, if packets (a) and (b) are not returned, but packet (c) is, assuming a single failure, it can quickly be determined that the failure is in PW8, PW9, or PW10.

One concern may be the size of the label stack that needs to be initially created. This concern normally arises in a forwarding context where a packet is received and the complete stack needs to be pushed. In one embodiment, most of the packets may be constructed in an OAM application with no labels being pushed or just the LSP label (e.g., 1002 in FIG. 4) being pushed in the forwarding subsystem.

If a PW is operating in FAT (Flow-Aware Transport) mode the testing TPE may need to push two labels (PW+FAT) (see, for example, IETF (Internet Engineering Task Force) RFC (Request for Comments) 6391, "Flow-Aware Transport of Pseudowire over an MPLS Packet Switched Network", S. Bryant et al., November 2011). If the TPE is using GAL (Generic Associated Channel Label) OAM, the GAL may be present only once at the bottom of stack. This may add some further complication in the forwarder as shown in the example below:

```
//Assume a TPE has just done the PW lookup at
//the top of stack
if (BOS-set)
__process-PW( ) // normal processing
__return
if (PW-FAT-enabled)
__if (FAT-label-BOS-set( ))
__process-PW( ) // normal FAT processing
__return
__else
__pop-FAT( )
// at this point what follows is another
// label, and it's either GAL or another
// PW label
if (GAL-TOS( ))
__process-OAM( )
__return
//It must be an MPLS forwarding label
forward-packet-using-TOS-label( )
return
// All done
```

The examples shown above do not need a Segment Routing (SR) control plane environment or SR specific labels. They may operate in classical MPLS/PW networks, and would also work in an SR environment.

The following describes an embodiment that may be used to avoid difficulties when the PW is not BoS. In this example, a control word (CW) is included and used to isolate the top label from the rest of the source routing information. A bit in the CW may be included or first nibble=2 may be used to indicate that the CW is followed by the source route and not a PW payload. This would also allow for the placing of the LSP+PW label pairs in the originating packet to save the recursive lookup needed if just the PW labels are carried.

Although the method and apparatus have been described in accordance with the embodiments shown, one of ordinary skill in the art will readily recognize that there could be variations made to the embodiments without departing from the scope of the invention. Accordingly, it is intended that all matter contained in the above description and shown in the accompanying drawings shall be interpreted as illustrative and not in a limiting sense.

What is claimed is:

1. A method comprising:
   building a concatenated communication path from a set of communication paths extending between a first network device and a second network device and terminating at one end at said first network device and at an opposite end at said second network device;
   generating at said first network device, a continuity test packet configured to pass through said set of communication paths;
   transmitting at said first network device, the continuity test packet on a first communication path in said set of communication paths;

receiving at said first network device, the continuity test packet on a second communication path in said set of communication paths and forwarding the continuity test packet from said first network device on a third communication path in said set of communication paths; and identifying at said first network device, a failure in said set of communication paths if the continuity test packet is not received on a last communication path in said set of communication paths.

2. The method of claim 1 wherein said set of communication paths comprises a plurality of virtual communication paths.

3. The method of claim 2 wherein said set of communication paths comprises a plurality of pseudowires.

4. The method of claim 3 wherein the network device comprises a terminating provider edge device.

5. The method of claim 1 wherein said set of communication paths comprises a plurality of physical communication paths.

6. The method of claim 1 wherein the network device operates in a Multi-Protocol Label Switching (MPLS) network and said set of communication paths comprises a plurality of Label Switched Paths (LSPs).

7. The method of claim 1 further comprising processing the received continuity test packet at the network device, wherein processing comprises popping a label in the continuity test packet with a bottom of stack bit clear and forwarding the continuity test packet to a next label in a label stack in the continuity test packet, wherein the label stack is configured so that the continuity test packet travels along the set of communication paths to be tested.

8. The method of claim 1 further comprising transmitting a second continuity test packet on a second set of communication paths terminating at the network device.

9. The method of claim 8 wherein said first and second set of communication paths comprise at least one communication path in common.

10. The method of claim 1 further comprising identifying a failure in said set of communication paths and transmitting at least two new continuity test packets to identify a failed communication path.

11. The method of claim 10 wherein three new continuity test packets are transmitted and one of said new continuity test packets is transmitted on a set of operating communication paths.

12. An apparatus comprising:
a plurality of interfaces for communication with a plurality of communication paths terminating at the apparatus and at least one other network device located at an opposite end of said communication paths; and
a processor for building a concatenated communication path from a set of communication paths extending between a first network device and a second network device and terminating at one end at said first network device and at an opposite end at said second network device, generating a continuity test packet configured to pass through said set of communication paths, transmitting the continuity test packet on a first communication path in said set of communication paths, receiving at said first network device, the continuity test packet on a second communication path in said set of communication paths and forwarding the continuity test packet from said first network device on a third communication path in said set of communication paths, and identifying a failure in said set of communication paths if the continuity test packet is not received on a last communication path in said set of communication paths.

13. The apparatus of claim 12 wherein said plurality of interfaces comprises virtual interfaces and said set of communication paths comprises a plurality of pseudowires.

14. The apparatus of claim 12 wherein said set of communication paths comprise a plurality of physical communication paths.

15. The apparatus of claim 12 wherein said set of communication paths comprises a plurality of tunnels.

16. The apparatus of claim 12 wherein the apparatus comprises a hub and said at least one other network device comprises a plurality of spokes, one or more of said communication paths in communication with each of said spokes.

17. The apparatus of claim 12 wherein the processor when operating at the apparatus, identifies a failure in said set of communication paths and transmits at least two new continuity test packets to identify a failed communication path.

18. Logic encoded on a non-transitory computer readable media and when executed by a processor operable to:
build a concatenated communication path from a set of communication paths extending between a first network device and a second network device and terminating at one end at said first network device and at an opposite end at said second network device
generate a continuity test packet configured to pass through said set of communication paths;
transmit the continuity test packet on a first communication path in said set of communication paths;
process at said first network device, the continuity test packet received on a second communication path in said set of communication paths and forward the continuity test packet from said first network device on a third communication path in said set of communication paths; and
identify a failure in said set of communication paths if the continuity test packet is not received on a last communication path in said set of communication paths.

19. The logic of claim 18 wherein said set of communication paths comprises a plurality of pseudowires and the continuity test packet comprises a plurality of labels corresponding to said plurality of pseudowires.

20. The apparatus of claim 13 wherein the apparatus is configured to test the pseudowires in a batch without the use of a control plane.

* * * * *